United States Patent [19]
Zahler et al.

[11] Patent Number: 5,272,152
[45] Date of Patent: Dec. 21, 1993

[54] PURINYL AND PYRIMIDINYL TETRAHYDROFURANS

[75] Inventors: Robert Zahler, Princeton, N.J.; Val S. Goodfellow, Morrisville, Pa.

[73] Assignee: E. R. Squibb & Sons, Inc., Princeton, N.J.

[21] Appl. No.: 719,861

[22] Filed: Jun. 24, 1991

Related U.S. Application Data

[63] Continuation-in-part of Ser. No. 546,957, Jul. 2, 1990, abandoned.

[51] Int. Cl.$^5$ ............... A61K 31/52; A61K 31/505; C07D 473/18; C07D 473/34
[52] U.S. Cl. ...................... 514/262; 514/81; 514/266; 544/244; 544/265; 544/276; 544/277; 544/313; 544/314; 544/317
[58] Field of Search ............ 544/255, 265, 276, 277; 514/81, 262, 266

[56] References Cited

U.S. PATENT DOCUMENTS

| | | | |
|---|---|---|---|
| 4,543,255 | 9/1985 | Shealy et al. | 514/258 |
| 4,758,572 | 7/1988 | Spector et al. | 514/265 |
| 4,849,412 | 7/1989 | Albrecht et al. | 514/46 |
| 5,032,680 | 7/1991 | Kawai et al. | 536/23 |
| 5,059,690 | 10/1991 | Zahler | 544/277 |
| 5,126,347 | 6/1992 | Huryn | 544/277 |

FOREIGN PATENT DOCUMENTS

| | | |
|---|---|---|
| 383239 | 8/1990 | European Pat. Off. |
| 391411 | 10/1990 | European Pat. Off. |
| 394893 | 10/1990 | European Pat. Off. |
| 57-146798 | 9/1982 | Japan |

OTHER PUBLICATIONS

Imai et al., Chem. Abst. vol. 66, 115923h (1967).
Montgomery et al., "Isonucleosides . . . ", J. Org. Chem. vol. 43, No. 4, pp. 541-544 (1978).
Huryn et al., "Synthesis of Iso-DDA . . . ", Tetrahedron Letters, vol. 30, No. 6, pp. 6259-6262 (1989).
Montgomery et al., "Isonucleosides . . . ", Abstracts of Papers of the Amer. Chem. Soc. vol. 173, Abstract 64, Med. Chem., (1977).
Reist, "Adenine Nucleosides of Branched Chain Sugars", Chemistry & Industry, (Nov. 1967), pp. 1957-1958.
Reist et al., "Branched Chain Sugars . . . ", Jour. Amer. Chem. Soc., 90:14, (1968), pp. 3852-3857.
Montgomery et al., "Isonucleosides I . . . ", Jour. Org. Chem., vol. 1975, pp. 1923-1927.
Ueda et al., "Chemical Conversion Of Nucleosides . . . ", Nucleic Acids Research, Symposium 9, 1981, pp. 91-94.
Shuto et al., "Chemical Conversion of Uridine . . . ", Nucleosides & Nucleotides, 1(3), 263-273, 1982.
Rosenthal et al., "Branched-chain Sugar Nucleosides . . . ", Canadian Jour. of Chem., vol. 47, 4477-4481 (1969).
Action et al., "Improved Antitumor Effects . . . ", Jour. of Medicinal Chem., (1979), vol. 22, pp. 518-525.

*Primary Examiner*—Mark L. Berch
*Attorney, Agent, or Firm*—Stephen B. Davis

[57] ABSTRACT

Antiviral activity is exhibited by compounds having the formula

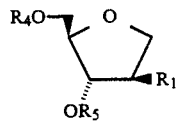

and its pharmaceutically acceptable salts.

9 Claims, No Drawings

PURINYL AND PYRIMIDINYL TETRAHYDROFURANS

RELATED APPLICATIONS

This application is a continuation-in-part of Ser. No. 546,957 filed Jul. 2, 1990, now abandoned.

BRIEF DESCRIPTION OF THE INVENTION

Antiviral acitivity is exhibited by compounds having the formula

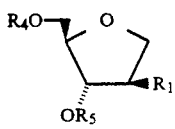

and its pharmaceutically acceptable salts. In formula 1, and throughout the specification, the symbols are as defined below.

$R_1$ is

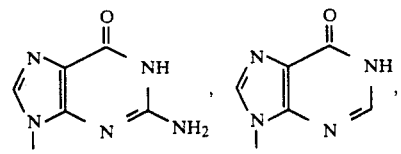

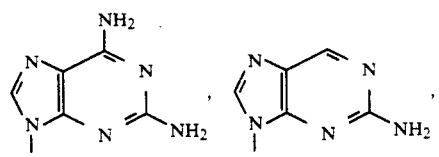

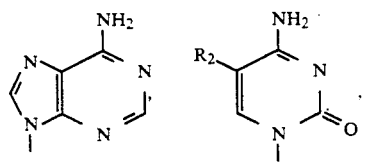

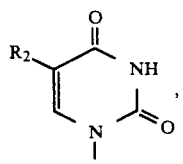

wherein $R_2$ is hydrogen, methyl, fluoro, chloro, bromo, iodo, trifluoromethyl, ethyl, n-propyl, 2-fluoroethyl, 2-chloroethyl or

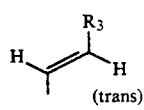

wherein $R_3$ is chloro, bromo, iodo, hydrogen, methyl or trifluoromethyl; $R_4$ and $R_5$ are independently hydrogen, $-PO_3H_2$ or $COR_6$; and $R_6$ is hydrogen, alkyl, substituted alkyl, or aryl.

Preferred compounds of formula 1 are those wherein $R_1$ is

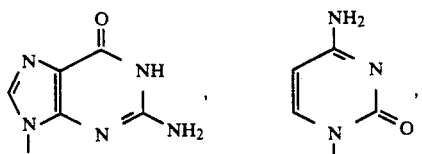

or

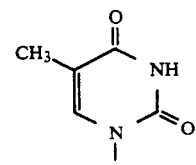

The most preferred compound of formula 1 is when $R_1$ is

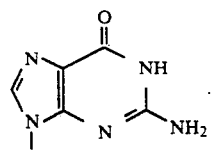

The term "alkyl" refers to both straight and branched chain groups. Those groups having 1 to 10 carbons are preferred. The term "substituted alkyl" refers to alkyl groups having one or more substituents. Preferred substituents are halogen, amino, amido, azido, hydroxy, cyano, trialkylammonium (wherein each alkyl group has 1 to 6 carbons), aryl and carboxy. The term "aryl" refers to phenyl and phenyl substituted with one, two or three substituents. Preferred substituents are alkyl (of 1 to 6 carbons), alkoxy (of 1 to 6 carbons), halogen, trifluoromethyl, amino, amido, alkylamino, dialkylamino, nitro, cyano, alkanoyloxy (of 2 to 11 carbons), carboxy, carbamoyl and hydroxy.

DETAILED DESCRIPTION OF THE INVENTION

The compounds of formula 1 and the pharmaceutically acceptable salts thereof, are antiviral agents that can be used to treat viral infections in mammalian species such as domesticated animals (e.g., dogs, cats, horses, cattle and the like) and humans, as well as in avian species (e.g. chickens and turkeys). The compounds of formula 1 wherein $R_1$ is

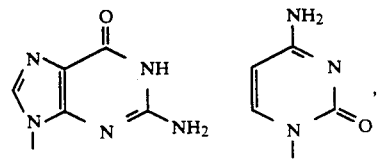

or

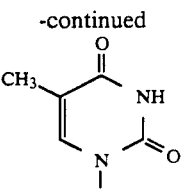

are effective against one or more of the following viruses: herpes simplex virus types 1 and 2 and varacella-zoster virus. They are also believed to be active against a variety of other DNA viruses. Exemplary DNA viruses in addition to those named above include other herpes viruses (e.g. Epstein-Barr virus, human herpes virus 6, pseudorabies virus, and the like), poxviruses (e.g. vaccinia, monkey pox and myoma), papovaviruses (e.g. the papilloma viruses), hepatitus B virus, and adenoviruses. All of the other compounds of formula 1 are believed to be active against one or more of the following viruses: herpes simplex virus types 1 and 2, varicella-zoster virus, cytomegalovirus, and the other DNA viruses described above.

The compounds of this invention may be administered parenterally (for example, by intravenous, intraperitoneal or intramuscular injection), orally or topically. The compounds may be administered orally or parenterally in an amount effective to treat the infection. The dosage will depend on the severity of infection, but will likely be in the range of 1 to 50 mg/kg body weight. The desired dose may be administered several times daily at appropriate intervals.

For infections of the eye, or other external tissues, (e.g. mouth and skin) the composition may be applied to the infected part of the body of the patient topically as an ointment, cream, aerosol, gel, powder, lotion, suspension or solution (e.g., as eye drops). The concentration of the compound in the vehicle will depend on the severity of the infection but will likely be in the range from about 0.1 to 7% by weight.

A compound of formula 1 can be prepared from an intermediate of formula

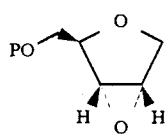

or an intermediate of formula

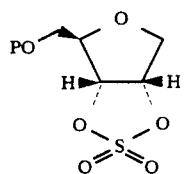

wherein P is a hydroxy protecting group such as benzyl, silyl [e.g., a hindered trisubstituted silyl such as t-butyldiphenylsilyl, (triphenylmethyl)dimethylsilyl, methyldiisopropylsilyl or triisopropylsilyl], trityl, or substituted trityl e.g., 4-monomethoxytrityl or 4,4'-dimethoxytrityl].

A compound of formula 2 can be synthesized from a compound of formula

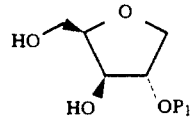

wherein $P_1$ is an acyl protecting group such as acetyl or benzoyl. The compound of formula 3 wherein $P_1$ is acetyl is known in the art. (J. A. Montgomery and J. Thomas, *J. Org. Chem.*, 43, 541 (1978)). The primary hydroxyl of compound 3 can be protected by methods known in the art with a group P to give a compound of formula

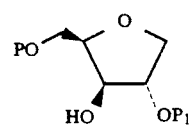

wherein P is chosen such that $P_1$ can be selectively removed in the presence of P. For example, P can be a benzyl, trityl, substituted trityl, or silyl group. The free hydroxyl group of compound 4 can be converted to a leaving group $X_1$, such as methanesulfonate, p-toluenesulfonate, or trifluoromethanesulfonate, by methods known in the art to give a compound of formula

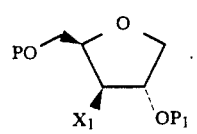

A compound of formula 5 can then be converted to a compound of formula 2 by selective removal of the $P_1$ protecting group and base promoted epoxide formation. For example, conversion of compound 5 to compound 2 can be achieved using potassium carbonate in methanol or ethanol, sodium methoxide in methanol, sodium ethoxide in ethanol, or sodium or potassium hydroxide in aqueous tetrahydrofuran or aqueous dioxane.

A compound of formula 26 can be prepared from a compound of the formula

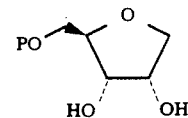

by method known in the art (Y. Gao and K. B. Sharpless, *J. Amer. Chem. Soc.*, 110, 7538(1988)).

The compound of formula 27 can be prepared by selective protection of the primary hydroxy group of the compound of formula

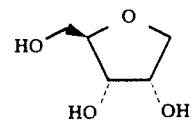

by methods known in the art. The compound of formula 28 is known in the art. (F. Weygard and F. Wirth, *Chem. Ber.*, 85, 1000 (1952)).

Reaction of a compound of formula 2 or 26 with a suitably protected form of guanine such as a compound of formula

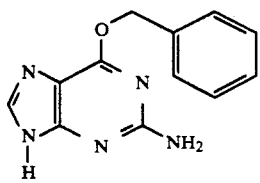

in the presence of a base such as lithium hydride, sodium hydride, potassium hydride, or potassium carbonate in an aprotic polar solvent such a dimethylformamide, dimethyl sulfoxide, or sulfolane (tetramethylene sulfone) yields, upon workup, the compound of formula

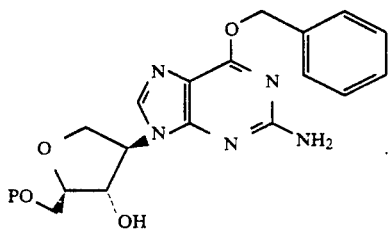

Optionally, the reaction can be run in the presence of appropriate metal chelating agents such as 18-crown-6 (1,4,7,10,13,16-hexaoxacyclooctadecane) or 15-crown-5 (1,4,7,10,13-pentaoxacyclopentadecane), or 12-crown-4 (1,4,7,10-tetraoxacyclododecane). Removal of the protecting groups from a compound of formula 7 yields the compound of formula 1 wherein $R_1$ is

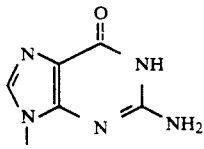

and $R_4$ and $R_5$ are hydrogen.

When the protecting group P in 7 is benzyl, simultaneous removal of the P group and the purine O-benzyl group can be effected by using sodium in liquid ammonia, by hydrogenolysis (e.g., palladium hydroxide on carbon, cyclohexene, and ethanol), or by using boron trichloride in dichloromethane. Alternatively, the purine O-benzyl group can be removed first using aqueous alcoholic mineral acid followed by removal of the P group using, for example, sodium in liquid ammonia or hydrogenolysis.

When the protecting group P is a silyl protecting group, removal of the P group can be accomplished using fluoride ion (e.g., tetrabutylammonium fluoride in tetrahydrofuran). The purine O-benzyl group can then be removed with aqueous alcoholic mineral acid, by hydrogenolysis, or with sodium in liquid ammonia. Alternatively, the purine O-benzyl group can be deprotected first by hydrogenolysis followed by removal of the silyl P group using fluoride ion.

When the protecting group P is a trityl or substituted trityl group, removal of the P group and the purine O-benzyl group can be accomplished simultaneously using aqueous/alcoholic mineral acid.

Reaction of the compound of formula 2 or 26 with a compound of formula

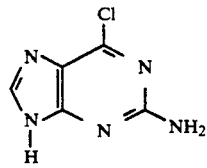

under conditions analogous to those used in the preparation of compound 7 provides, upon workup, a compound of formula

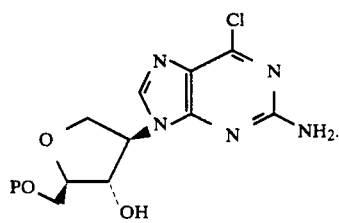

A compound of formula 1 wherein $R_1$ is

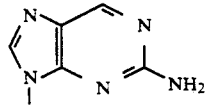

and $R_4$ and $R_5$ are hydrogen can be prepared from a compound of formula 9. For example, when the P group in 9 is benzyl, deprotection and reduction of the chloro group can be accomplished simultaneously by hydrogenation (e.g., ammonium formate and palladium on carbon in methanol; palladium hydroxide on carbon, cyclohexene and ethanol; or palladium on carbon, hydrogen and ethanol). When the P group is silyl the chloro group can first be reduced by hydrogenation and then the protecting group can be removed using fluoride ion. Alternatively, the silyl protecting group can be removed first and then the chloro group can be reduced. When the P group is trityl or substituted trityl, deprotection of the P group can be effected using aqueous acid and the chloro group can then be reduced by hydrogenation.

Alternatively, this compound of formula 1 can be prepared by reacting an optionally protected compound of formula

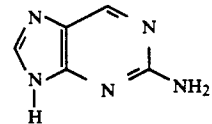

with a compound of formula 2 or 26 according to the procedures analogous to those used in the preparation of a compound of formula 7, followed by removal of the protecting group(s) by methods known in the art. The optionally protected forms of compound 10 can be protected at the amino (—NH$_2$) group by such exemplary groups as acyl (e.g., acetyl or benzoyl), trityl, or substituted trityl.

A compound of formula 1 wherein $R_1$ is

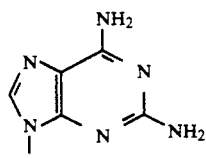

5 and $R_4$ and $R_5$ are hydrogen can be prepared from a compound of formula 9 by methods known in the art (e.g., J. C. Martin, et. al., *J. Med. Chem.*, 28, 358 (1985)). Thus, for example, when a compound of formula 9 is treated with hot methanolic ammonia, displacement of the chloro group with an amino group will result. When the protecting group P is a benzyl group, subsequent deprotection can be accomplished by hydrogenolysis, by sodium in liquid ammonia, or by using boron trichloride. When the protecting group P is a silyl group, subsequent deprotection can be accomplished using fluoride ion. When the protecting group is a trityl or substituted trityl group, subsequent deprotection can be accomplished using aqueous acid.

Alternatively, this compound of formula 1 can be prepared by reacting an optionally protected compound of formula

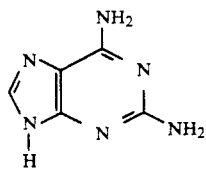

11 with a compound of formula 2 or 26 according to the procedures analogous to those used in the preparation of a compound of formula 7, followed by removal of the protecting group(s) by methods known in the art. An optionally protected form of 11 can be protected at the amino (—NH2) groups by such exemplary groups as trityl, substituted trityl or acyl (e.g. acetyl or benzoyl).

Reaction of the compound of formula 2 or 26 with a compound of formula

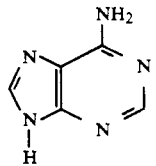

12 by methodology analogous to that used to prepare a compound of formula 7, and subsequent removal of the P protecting group, yields the corresponding compound of formula 1 wherein $R_1$ is

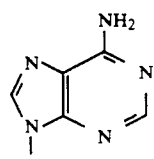

and $R_4$ and $R_5$ are hydrogen.

Alternatively, this compound of formula 1 can be prepared by reaction of a compound of formula

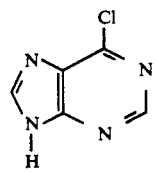

13 with a compound of formula 2 or 26 by method analogous to those used in the preparation of a compound of formula 7. This affords the corresponding compound of formula

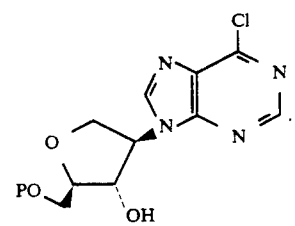

14

Treatment of a compound of formula 14 with hot ammonia in an alcohol (such as methanol or ethanol) and subsequent removal of the P protecting group yields the corresponding compound of formula 1 wherein $R_1$ is

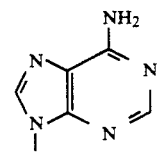

and $R_4$ and $R_5$ are hydrogen.

Reaction of the compound of formula 2 or 26 with a compound of formula

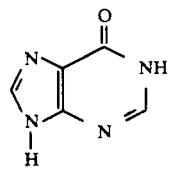

15 by methodology analogous to that used to prepare a compound of formula 7 and subsequent removal of the protecting group P yields the corresponding compound of formula 1 wherein $R_1$ is

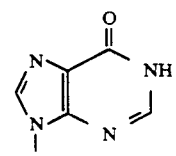

and $R_4$ and $R_5$ are hydrogen.

Alternatively, this compound of formula 1 can be prepared by treatment of the compound of formula 1 wherein $R_1$ is

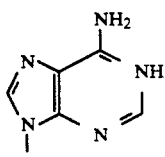

and R$_4$ and R$_5$ are hydrogen with adenosine deaminase or nitrous acid.

Alternatively, this compound of formula 1 can be prepared from a compound of formula 14 by removal of the P protecting groups and subsequent (or simultaneous) hydrolysis of the chloro group. For example, when P is a benzyl group, this group can be selectively removed with boron trichloride. Subsequent hydrolysis of the chloro group can be achieved using acid (e.g. aqueous hydrochloric acid) or base (e.g. aqueous methanolic sodium hydroxide). When P is a silyl protecting group, this group can be selectively removed with fluoride, followed by hydrolysis of the chloro group, or the silyl and chloro groups can be removed simultaneously under the hydrolysis conditions. When P is a trityl or substituted trityl group, the P protecting group and the chloro group can be removed simultaneously using acid hydrolysis.

The compound of formula

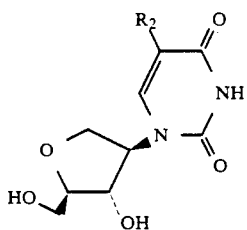

wherein R$_2$ is hydrogen, fluoro, methyl, ethyl, n-propyl, or 2-fluoroethyl can be prepared by reaction of the corresponding compound of formula

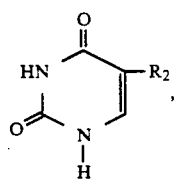

with a compound of formula 2 or 26 in the presence of a base such as potassium carbonate, lithium hydride, sodium hydride, or potassium hydride, in an aprotic polar solvent (e.g., dimethylformamide, dimethyl sulfoxide or sulfolane), in the optional presence of 18-crown-6, 15-crown-5 or 12-crown-4, to yield, upon workup, an intermediate of formula

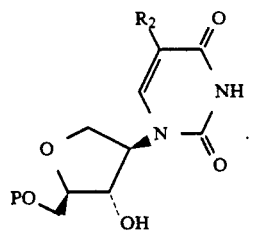

Removal of the protecting group P provides the corresponding compound of formula 16.

For example, when P is benzyl, this protecting group can be removed by hydrogenolysis (e.g. palladium hydroxide on carbon, cyclohexene and ethanol) or by treatment with boron trichloride. When P is silyl, deprotection can be accomplished with fluoride ion. When P is trityl or substituted trityl, deprotection can be accomplished with aqueous acid.

The compound of formula 17 wherein R$_2$ is 2-fluoroethyl can be prepared by methods known in the art [H. Griengl, et al. *J. Med. Chem.*, 30, 1199 (1987)].

The compound of formula 16 wherein R$_2$ is fluoro can also be prepared from the corresponding compound 16 wherein R$_2$ is hydrogen and the hydroxy groups are optionally protected with a group such as acyl (e.g., acetyl or benzoyl) by fluorination with trifluoromethyl hypofluorite using methodology known in the art. For example, see M. J. Robins, et al., *J. Amer. Chem. Soc.*, 93, 5277 (1971) and *Chem. Commun.*, 18 (1972); T. S. Lin, et al., *J. Med. Chem.*, 26, 1691 (1983).

The compounds of formula 16 wherein R$_2$ is 2-chloroethyl and 2-fluoroethyl can be prepared from a compound of formula

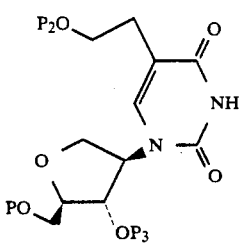

wherein P, P$_2$ and P$_3$ are protecting groups wherein P$_2$ can be selectively removed in the presence of P and P$_3$. Protecting groups P and P$_3$ may be the same or different. For example, when P$_2$ is a silyl group, P can be trityl, substituted trityl or benzyl and P$_3$ can be trityl, substituted trityl, benzyl or acyl (e.g., acetyl or benzoyl). Alternatively, when P$_2$ is an acyl group, P and P$_3$ can be independently trityl, substituted trityl, silyl or benzyl. Alternatively, when P$_2$ is a trityl or substituted trityl group, P can be silyl or benzyl and P$_3$ can be silyl, benzyl or acyl. Selective removal of the protecting group P$_2$ yields a compound having the formula

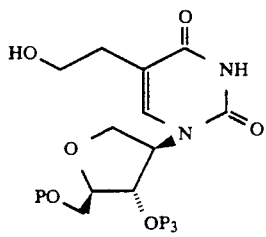

20

Treatment of compound of formula 20 with triphenylphosphine-carbon tetrachloride or diethylaminosulfur trifluoride, and subsequent removal of protecting groups P and $P_3$, affords the compound having the formula 16 wherein $R_2$ is 2-chloroethyl or 2-fluoroethyl, respectively. Alternatively, treatment of a compound 20 with triphenylphosphine/N-bromosuccinimide, triphenylphosphine/N-bromosuccinimide/-tetrabutylammonium iodide or para-toluenesulfonyl chloride/pyridine (see H. Griengl, et al., *J. Med. Chem.*, 28, 1679 (1985)) affords compounds having the formula

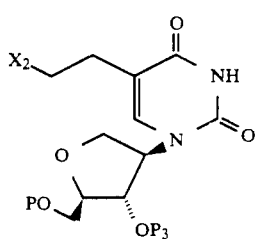

21 wherein $X_2$ z is bromo, iodo or para-toluenesulfonate respectively. Subsequent treatment with fluoride ion, followed by removal of protecting groups P and $P_3$, provides the compound of formula 16 wherein $R_2$ is 2-fluoroethyl.

The compound of formula 19 can be prepared by reaction of a compound of formula

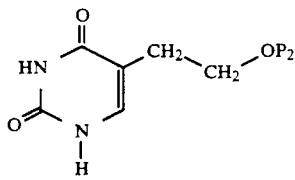

22 with a compound of formula 2 or 26 by methods analogous to those used for the preparation of 18 (wherein, for example, $R_2$ is hydrogen, methyl or ethyl) followed by protection with the $P_3$ group by methods known in the art. The compound of formula 22 can be prepared from the corresponding free alcohol by methods known in the art.

The compounds of the formula

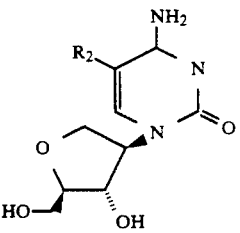

23 wherein $R_2$ is hydrogen, fluoro, methyl, ethyl, n-propyl, 2-chloroethyl, or 2-fluoroethyl can be prepared from the corresponding compounds of formula

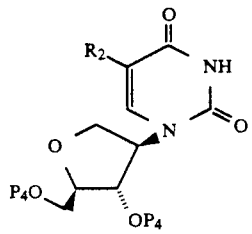

24 wherein $P_4$ is a protecting group such as acyl, (e.g., acetyl or benzoyl) by methods known in the art. See, for example, I. Wempner, et al. in "Synthetic Procedures in Nucleic Acid Chemistry", Vol. 1, W. W. Zorbach and R. S. Tipson, Eds., Interscience Publishers, N.Y., p. 299, 1968; W. L. Sung, *J. Org. Chem.*, 47, 3623 (1982); T. S. Lin, et al., *J. Med. Chem.*, 26, 1961 (1983); P. Herdewijn, et al., *J. Med. Chem.*, 28, 550 (1985); European Patent No. 204,264A (1985). The compound of formula 24 can be prepared from the corresponding compound of formula 16 by methods known in the art.

Alternatively, the compound of formula 23, wherein $R_2$ is fluoro, hydrogen, methyl, ethyl, n-propyl or 2-fluoroethyl, can be prepared by reaction of the corresponding compound of formula

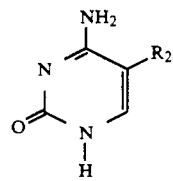

25 with a compound of formula 2 or 26 in the presence of a base such as potassium carbonate, lithium hydride, sodium hydride, or potassium hydride in an aprotic solvent (e.g. dimethylformamide, dimethyl sulfoxide or sulfolane), in the optional presence of 18-crown-6, 15-crown-5 or 12-crown-4, and subsequent removal of the protecting group P. Optionally, the amino (—NH$_2$) group in 25 can be protected, e.g., with an acyl group. Removal of this protecting group can be accomplished using sodium methoxide in methanol or methanolic ammonia.

Alternatively, the compound of formula 23 wherein $R_2$ is fluoro can be prepared from the corresponding compound wherein $R_2$ is hydrogen by fluorination with trifluoromethyl hypofluorite using methodology known in the art. Fluorination can also be performed on the compounds of formula 23 wherein $R_2$ is hydrogen and the hydroxyl and/or amino groups are protected, for example, by an acyl group such as acetyl or benzoyl. After fluorination, deprotection of the acyl groups using methanolic ammonia or aqueous hydroxide affords the compound of formula 23 wherein $R_2$ is fluoro. See, for example, M. J. Robins, et al., *J. Amer. Chem. Soc.*, 93, 5277 (1971) and *Chem. Commun.*, 18 (1972); T. S. Lin, et al., *J. Med. Chem.*, 26, 1691 (1983).

The compounds of formula 16 and 23 wherein $R_2$ is chloro, bromo or iodo can be prepared from the corresponding compounds of formula 16 and 23 wherein $R_2$ is hydrogen by methods known in the art. See, for example, "Basic Principals in Nucleic Acid Chemistry", Vol. 1, P.O.P. Ts'O, Ed., Academic Press, N.Y., P. 146, 1974; P. K. Chang in "Nucleic Acid Chemistry" Part 3, L. B. Townsend and R. S. Tipson, Eds., John Wiley and Sons, N.Y. p.46, 1986.

The compounds of formula 16 and 23 wherein $R_2$ is trifluoromethyl can be prepared from the corresponding compounds of formula 16 and 23 wherein $R_2$ is iodo and the hydroxy and amino (—$NH_2$) groups are protected, for example, by an acyl group (e.g., acetyl or benzoyl) by treatment with trifluoromethyl iodide and copper according to procedures known in the art. Subsequent deprotection using methanolic ammonia or sodium methoxide in methanol yields the corresponding compound of formulas 16 and 23 wherein $R_2$ is trifluoromethyl. See, for example, Y. Kobayashi, et al., *J. Chem. Soc. Perkin* 1, 2755 (1980); S. Lin, et al., *J. Med. Chem.*, 26, 1691 (1983).

The compounds of formula 16 and 23 wherein $R_2$ is

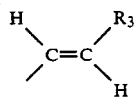

and $R_3$ is chloro, bromo, iodo, hydrogen, methyl or trifluoromethyl can be prepared from the corresponding compounds of formula 16 and 23 wherein $R_2$ is iodo or —HgCl via organopalladium intermediates. The compounds of formula 16 and 23 wherein $R_2$ is —HgCl can be prepared from the corresponding compounds of formula 16 and 23 wherein $R_2$ is hydrogen by methods known in the art. See, for example, M. E. Perlman, et al., *J. Med. Chem.*, 28, 741 (1985); P. Herdewijn, et al., *J. Med. Chem.*, 28, 550 (1985); D. E. Bergstrom, et al., *J. Med. Chem.*, 27, 279 (1984); and references in E. DeClercq, et al., *Pharmac. Ther.*, 26, 1 (1984).

Compounds of formula 1 wherein one or both $R_4$ and $R_5$ are

can be prepared by methods known in the art from the corresponding compounds of formula 1 wherein $R_4$ and $R_5$ are hydrogen.

For examples of acylation procedures see: "Synthetic Procedures in Nucleic Acid Chemistry", Vol. 1, W. W. Zorbach and R. S. Tipson, Eds., John Wiley and Sons, 1968; "Nucleic Acid Chemistry," Part 1, L. B. Townsend and R. S. Tipson, Eds., John Wiley and Sons, 1978; Y. Ishido, et al., *Nucleosides and Nucleotides*, 5, 159 (1986); J. C. Martin, et al., *J. Pharm. Sci.*, 76, 180 (1987); A. Matsuda, et al., *Synthesis*, 385 (1986).

Compounds of the formula 1 wherein $R_4$ and/or $R_5$ are —$PO_3H_2$ can be prepared from the corresponding compounds of formula 1 wherein $R_4$ and $R_5$ are hydrogen by procedures known in the art. See, for example, H. Schaller, et al., *J. Amer. Chem. Soc.*, 85, 3821 (1963); J. Beres, et al., *J. Med. Chem.*, 29, 494 (1986); R. Noyori, et al., *Tet. Lett.*, 28, 2259 (1987); W. Pfeiderer, et al., *Helv. Chim. Acta.*, 70, 1286 (1987); "Nucleic Acid Chemistry". Part 2, L. B. Townsend and R. S. Tipson, Eds., John Wiley and Sons, 1978.

The stereochemistry shown for the compounds of this invention is absolute. It is drawn to show that in the compounds of this invention, the absolute stereochemistry is derived from the chiral precursors, D-sorbitol or 1,4-anhydro-D-ribitol.

The compounds of formula 1 wherein $R_1$ is

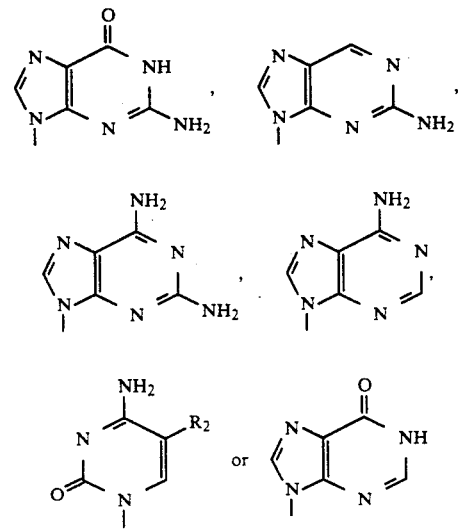

can form acid addition salts with inorganic or organic acids. Illustrative are the halide (e.g., chloride and bromide), alkylsulfonate, sulfate, phosphate and carboxylate salts.

The compounds of formula I wherein $R_1$ is

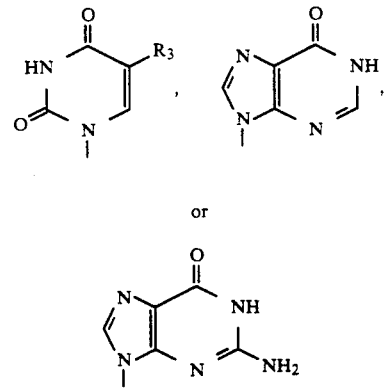

can form basic salts with inorganic and organic bases. Illustrative are alkali metal salts (e.g., sodium and potassium), alkaline earth metal salts (e.g., calcium and magnesium), ammonium and substituted ammonium salts.

The compounds of formula 1 wherein $R_4$ and/or $R_5$ are —$PO_3H_2$ can form basic salts with inorganic and organic bases. Illustrative are the alkali metal salts (e.g., sodium and potassium), alkaline earth metal salts (e.g., calcium and magnesium), ammonium and substituted ammonium salts.

The following examples are specific embodiments of this invention. All temperatures are given in degrees Centigrade.

EXAMPLE 1

[3R-(3α,4β,5α)]-2-Amino-1,9-dihydro-9-tetrahydro-4-hydroxy-5-(hydroxymethyl)-3-furanyl]-6H-purin-6-one

A.

[2R-[2α(S*),3α,4β]]-Tetrahydro-β,3,4-trihydroxy-2-furanethanol

This was prepared by modification of the method of S. Soltzberg (J. Amer. Chem. Soc., 68 919 (1946)). In a 500 ml round bottom flask, D-Sorbitol (10.0 g, 54.9 mmole) was added to a solution of 110 mg of concentrated $H_2SO_4$ in 1.5 ml $H_2O$. The flask was warmed in a 100° oil bath until the solid began to melt. The flask was then evacuated (approximately 18 mm Hg) and placed in a 140° oil bath. The reaction stirred at 135°-145° for 25 minutes at reduced pressure. The reaction flask was cooled to room temperature, 50 ml of $H_2O$, and approximately 5 g of Norit were added. The flask was warmed in a 100° oil bath for three minutes and the mixture was filtered. After cooling to room temperature, the filtrate was neutralized with barium acetate to pH 7, and allowed to stand for one hour. The precipitate was then removed by filtration, and the solvent was removed to provide a viscous syrup (10 g). A portion of this syrup (8.0 g) was suspended in 100 ml of 2-propanol and filtered. The filtrate was concentrated and purified by chromatography on silica gel (0-30% $CH_3OH$ in $CHCl_3$) to give 2.50 g of [2R-[2α(S*),3α,4β]]-tetrahydro-β,3,4-trihydroxy-2-furanethanol.

B.

[2S-(2α,3α,4β)]-Tetrahydro-3,4-dihydroxy-2-furancarboxaldehyde

This was prepared by modification of the original procedure reported by Hedgley (J. Am. Chem. Soc., 86 1576 (1964)). [2R-[2α(S*),3α,4β]]-tetrahydro-β,3,4-trihydroxy-2-furanethanol from Example 1A (1.90 g, 11.6 mmole) was suspended in 24 ml $H_2O$. A solution of 2.48 g of $NaIO_4$ in 30 ml $H_2O$ was added dropwise. After the addition was complete, the reaction was stirred for 3 hours at room temperature. The solvent was removed in vacuo, and the residue was triturated three times with hot ethanol (75°). The ethanol extracts were cooled and filtered. The solvent was concentrated by rotary evaporation to provide the crude title compound (1.85 g) as a colorless oil.

C.

[2R-(2α,3α,4β)]-Tetrahydro-3,4-dihydroxy-2-furanmethanol

[2S-(2α,3α,4β)]-Tetrahydro-3,4-dihydroxy-2-furancarboxaldehyde (1.85 g) was dissolved in 30 ml of $H_2O$ and treated in one portion with 300 mg $NaBH_4$. The reaction was stirred under a nitrogen atmosphere for 60 hours and was then acidified to pH 2 with AG MP-50(H+) ion exchange resin. The mixture was filtered, and the residue was washed with $H_2O$ and methanol. The combined filtrate was concentrated by rotary evaporation to a colorless syrup. Methanol (50 ml) was added and removed in vacuo. The addition and evaporation of methanol was repeated 5 times. The product was dried at 0.2 mm Hg to provide 1.51 g of the crude title compound as a colorless oil.

D.

[4aR-(4aα,7α,7aα)]-Tetrahydro-2,2-dimethyl-4H-furo[3,2-d]-1,3-dioxin-7-ol

A mixture of 100 ml of dry distilled acetone, 2,2-dimethoxypropane (5.83 g), and p-toluenesulfonic acid monohydrate (106 mg, 0.56 mmole) was added to crude [2R-(2α,3α,4β)]-tetrahydro-3,4-dihydroxy-2-furanmethanol (1.50 g, 11.2 mmole) with rapid stirring. The reaction was stirred 5 hours at room temperature under an argon atmosphere. The solution was chilled to 0°, and solid $NaHCO_3$ was added until wet pH paper indicated pH 7.5 for the solution. The solvent was then removed by rotary evaporation, and the residue was partitioned between chloroform and $H_2O$. The aqueous solution was extracted 7 times with equal volumes of $CHCl_3$, and the extracts were combined and concentrated to give 1.30 g of a colorless oil. Chromatography on silica gel (60 g, 1-3% $CH_3OH$ in $CHCl_3$) provided 901 mg of pure title compound as a colorless oil which solidified upon storage at 0°.

E.

[4aR-(4aα,7α,7aα)]-Tetrahydro-2,2-dimethyl-4H-furo[3,2-d]-1,3-dioxin-7-ol, acetate ester This was prepared according to the method of Montgomery (J. Org. Chem., 43, 541 (1978)). [4aR-(4aα,7α,7aα)]-Tetrahydro-2,2-dimethyl-4H-furo[3,2-d]-1,3-dioxin-7-ol (620 mg, 3.56 mmole) was dissolved in 2.3 ml of dry pyridine and chilled to 0° under argon. Acetic anhydride (0.67 ml) was added via syringe, and the cooling bath was removed. After stirring for 20 hours at room temperature, the reaction mixture was poured into 30 ml of saturated $NaHCO_3$ and 30 g crushed ice. This mixture was extracted three times with equal volumes of $CHCl_3$. The combined extracts were washed with saturated $NaHCO_3$ solution and three times with $H_2O$. The solution was dried over anhydrous $MgSO_4$ and concentrated. Residual solvent was removed by evacuating (ca. 5 mm Hg) at 70° C. for 45 minutes. This provided 620 mg of the title compound as a colorless syrup.

F.

[2R-(2α,3α,4β)]-Tetrahydro-3,4-dihydroxy-2-furanmethanol, 4-acetate ester

This was prepared according to the method of Montgomery (J. Org. Chem., 43, 541 (1978)). [4αR-(4aα,7α,7aα)]-Tetrahydro-2,2-dimethyl-4H-furo[3,2-d]-1,3-dioxin-7-ol, acetate ester (600 mg, 2.77 mmole) was dissolved in 14 ml of ethanol, chilled to 0°, and treated with 2.77 ml of 1N HCl. The reaction was allowed to warm to room temperature and stirred for approximately 4 hours. The solvent was removed in vacuo, and the residue was taken up in 30 ml of $CHCl_3$. The $CHCl_3$ solution was neutralized with solid $Na_2CO_3$, filtered, dried over $MgSO_4$, and concentrated in vacuo to provide 410 mg of the title compound as a colorless oil.

G.

[2R-(2α,3α,4β)]-Tetrahydro-2-[[(4-methoxyphenyl)diphenylmethoxy]methyl]-3,4-furandiol, 4-acetate ester Under an argon atmosphere, [2R-(2α,3α,4β)]-tetrahydro-3,4-dihydroxy-2-furanmethanol, 4-acetate ester (375 mg, 2.13 mmole) was dissolved in 11 ml of 10:1

CH$_2$Cl$_2$/dimethylformamide, chilled to 0°, and treated in one portion with 4-monomethoxytrityl chloride (658 mg, 2.13 mmole). A solution of triethylamine (0.44 ml, 3.2 mmole) in 1 ml of CH$_2$Cl$_2$ was added dropwise over two minutes with rapid stirring. The reaction was allowed to stir for four hours at 0°–5° and was then diluted with 15 ml of CH$_2$Cl$_2$. The methylene chloride solution was washed with saturated NaHCO$_3$ (1×20 ml) and H$_2$O (2×20 ml) and then dried over Na$_2$SO$_4$. The solvent was removed in vacuo, and the residue was chromatographed on 60 g of silica gel (eluting with 100 ml of hexane, followed by 1L of hexane: acetone (80:20)). Evaporation of the solvent and drying under high vacuum provided 847 mg of the title compound as a colorless foam.

H.
[2R-(2α,3α,4β)]-Tetrahydro-2-[[(4-methoxyphenyl)diphenylmethoxy]methyl]-3,4-furandiol, 4-acetate, 3-methanesulfonate ester All of the [2R-(2α,3α,4β)-tetrahydro-2-[[(4-methoxyphenyl)diphenylmethoxy]methyl]-3,4-furandiol, 4-acetate ester from Example 1G was dissolved under argon in 8.3 ml of dry pyridine and chilled to 0°. Methanesulfonyl chloride (0.30 ml, 3.9 mmole) was added via syringe, and the reaction mixture was allowed to warm to room temperature. After five hours, the reaction mixture was poured into a mixture of ice water and chloroform, and the resulting mixture was extracted twice with chloroform. The combined organic layers were washed twice with saturated NaHCO$_3$, three times with water, and dried over anhydrous MgSO$_4$. The solvent was removed under vacuum to yield 980 mg of a colorless foam which was used without further purification.

I.
[2R-(2α,3β,4β)]-3,4-Epoxytetrahydro-2-[[(4-methoxyphenyl)diphenylmethoxy]methyl]furan

[2R-(2α,3α,4β)]-Tetrahydro-2-[[(4-methoxyphenyl)diphenylmethoxy]methyl]-3,4-furandiol, 4-acetate, 3-methanesulfonate ester (930 mg, 1.76 mmole) was dissolved in 10 ml of dry methanol and treated with anhydrous K$_2$CO$_3$ (293 mg, 2.1 mmole). The reaction was carefully monitored by TLC (hexane:acetone 7:3) for the disappearance of the intermediate alcohol formed by methanolysis of the acetate. After 3 hours, the formation of epoxide appeared to be complete, and the solvent was removed under vacuum. The residue was partitioned between CHCl$_3$ and 5% NaHCO$_3$, and the aqueous layer was extracted with CHCl$_3$. The organic extracts were combined, dried over MgSO$_4$, and concentrated to a pale yellow syrup. Flash chromatography (30 g silica gel, 8:2 hexane:acetone) provided 565 mg of the title compound as a white foam.

J. 3R-(3α,4β,5β)]-6-(phenylmethoxy)-9-tetrahydro-4-hydroxy-5-[[(4-methoxyphenyl)diphenylmethoxy]methyl]-3-furanyl]-9H-purin-2-amine

[2R-(2α,3β,4β)]-3,4-Epoxytetrahydro-2-[[(4-methoxyphenyl)diphenylmethoxy]methyl]furan (520 mg, 1.34 mmole, dried three times azeotropically with toluene), 18-crown-6 (266 mg, 1.00 mmole), 6-(phenylmethoxy)-9H-purin-2-amine (549 mg, 2.27 mmole), and NaH (60% dispersion, 32.2 mg, 1.34 mmole) were suspended in 3 ml of dry sulfolane under argon, and the reaction vessel was placed in a 110° oil bath. The reaction was stirred under argon for 20 hours at 110°. The reaction mixture was cooled to room temperature, treated with 10 g silica gel, slurried in 15 ml of CH$_2$Cl$_2$, and applied to a column of silica gel (80 g) packed in CH$_2$Cl$_2$. This column was eluted slowly (using gravity) with 300 ml CH$_2$Cl$_2$, followed by a step gradient to 3% CH$_3$OH in CH$_2$Cl$_2$. Mixed fractions were rechromatographed to yield a total of 348 mg of the title compound as a pale yellow oil.

K.
[3R-(3α,4β,5α)]-2-Amino-1,9-dihydro-9-tetrahydro-4-hydroxy-5-(hydroxymethyl)-3-furanyl]-6H-purin-6-one

[3R-(3α,4β,5α]-6-(phenylmethoxy)-9-[tetrahydro-4-hydroxy-5-[[(4-methoxyphenyl)diphenylmethoxymethyl]-3-furanyl]-9H-purin-2-amine (300 mg, 0.476 mmole) was dissolved under nitrogen in 10 ml of methanol and 10 ml tetrahydrofuran. This mixture was treated with 5 ml of 3N HCl. The reaction vessel was placed in a 65° oil bath and heated at 65° for one hour under nitrogen atmosphere. After stirring 2 hours at room temperature, the solution was adjusted to pH 7.5 with solid NaHCO$_3$ and the solvent was removed under vacuum.

Reverse phase chromatography (CHP-20P resin, 75–150μ, Mitsubishi Chemical Co., eluting with water) provided 90 mg of the title compound as a white solid upon removal of the water under vacuum, followed by addition of methanol and concentration to dryness three times. M.P. 227° C. (dec.);

$^1$H-NMR (270 MHz, DMSO) δ7.72 (s, 1H), 6.63 (s, 2H), 5.74 (brs, 1H), 4.86 (brs, 1H), 4.62 (m, 1H), 4.28 (t, J=5.3 Hz), 4.11 (dd, J=9.4, 6.45, 1H) 3.93 (dd, J=9.4, 5.3 Hz, 1H), 3.50–3.70 (m, 3H).

EXAMPLE 2
[3R-(3α,4β,5α)]-5-Methyl-1-[tetrahydro-4-hydroxy-5-(hydroxymethyl)-3-furanyl]2,4(1H,3H)pyrimidinedione

A.
[2R-[2α(S*),3α,4β]]-Tetrahydro-β,3,4-trihydroxy-2-furanethanol

This was prepared by modification of the method of S. Soltzberg (J. Am. Chem. Soc., 68, 919 (1946)). In a 2L round bottom flask, D-Sorbitol (130 g) was added to a solution of 1.43 g of concentrated H$_2$SO$_4$ in 19.5 ml of H$_2$O. The flask was warmed in a 100° oil bath until the solid began to melt. The flask was then evacuated, maintained at approximately 20–25 mm Hg, and placed in a 140° oil bath. The reaction was stirred at 125°–145° for 30 minutes at reduced pressure. The reaction flask was then cooled to room temperature and 500 ml of H$_2$O and approximately 25 g of Norit were added. The flask was warmed in a 80° oil bath for several minutes and the mixture was filtered. After cooling to room temperature, the filtrate was neutralized with barium acetate to pH 6.5, and allowed to stand for one hour. The precipitate was then removed by filtration and the solvent was removed to provide a colorless, oily solid. Chromatography on silica gel (750 g 0–30% CH$_3$OH in CHCl$_3$) yielded 30.0 g of impure [2R-2α(S*),3α,4β]]-tetrahydro-β,3,4-trihydroxy-2-furanethanol, which was used as such in the following step.

B.
[4aR(4aα,7α,7aα)]-Tetrahydro-2,2-dimethyl-4H-furo[3,2-d]-1,3-dioxin-7-ol A portion of the oily mixture from Example 2A (23.3 g) was suspended in 250 ml of H$_2$O. A solution of 30.4 g of NaIO$_4$ in 300 ml of H$_2$O was added dropwise. After the addition was complete, the reaction was stirred for 3 hours at room temperature. The solvent was removed in vacuo, and the residue was triturated three times with hot ethanol (75°). The ethanol extracts were cooled and filtered. The solvent was concentrated by rotary evaporation to provide a 15.5 g of a colorless oil. This crude mixture was dissolved in 370 ml of $H_2O$ and treated with 5.0 g of $NaBH_4$. The reaction was stirred for approximately 15 hours at room temperature and was then acidified to pH 2 with AG MP-50 ($H^{30}$) ion exchange resin. The mixture was filtered, and the residue was washed well with $H_2O$ and methanol. The combined filtrates were concentrated by rotary evaporation to a colorless syrup. Methanol (500 ml) was added and removed in vacuo. The addition and evaporation of methanol was repeated 3 times. The product was dried at 0.5 mm Hg to provide 14.0 g of a colorless oil. The majority of this oil (13.9 g) was suspended in 900 ml of acetone, and p-toluenesulfonic acid monohydrate (982 mg, 5.12 mmole) and 2,2 dimethoxypropane (63.1 ml) were added under argon with stirring. The reaction was stirred for 4 hours at room temperature. Approximately 10 g of solid $NaHCO_3$ was added, and the solvent was removed in vacuo. The residue was suspended in a mixture of $CHCl_3$ and $H_2O$, and the mixture was extracted seven times with $CHCl_3$. The combined $CHCl_3$ extracts were dried over $MgSO_4$ and concentrated to a colorless oil. Chromatography on silica gel (450 g, 0-5% $CH_3OH$ in $CHCl_3$) provided 4.44 g of pure title compound as a colorless oil that solidified upon refrigeration.

C.

[4aR-(4a$\alpha$,7$\alpha$,7a$\alpha$)]-Tetrahydro-2,2-dimethyl-4H-furo[3,2-d]-1,3-dioxin-7-ol, acetate ester

[4aR-(4a$\alpha$,7$\alpha$,7a$\alpha$)]-Tetrahydro-2,2-dimethyl-4H-furo[3,2-d]-1,3-dioxin-7-ol (4.20 g, 24.1 mmole) was dissolved in 30 ml of ethyl acetate (under nitrogen) and treated with 4-dimethylaminopyridine 0.294 g, .241 mmole). Acetic anhydride (10 ml) was then added and the reaction stirred for one hour at room temperature. The reaction mixture was diluted with 120 ml of ethyl acetate and washed with saturated $NaHCO_3$ solution and brine. The ethyl acetate solution was dried over anhydrous $MgSO_4$ and concentrated. Residual solvent was removed by repeated concentration from toluene under vacuum. Final drying at ca. 5 mm Hg at 70° for 1 hour resulted in 3.70 g of the title compound as a colorless syrup.

D.

[2R-(2$\alpha$,3$\alpha$,4$\beta$)]-Tetrahydro-3,4-dihydroxy-2-furanmethanol, 4-acetate ester

[4aR-(4a$\alpha$,7$\alpha$,7a$\alpha$)]-etrTahydro-2,2-dimethyl-4H-furo[3,2-d]-1,3-dioxin-7-ol (3.70 g) was dissolved in 90 ml of ethanol, chilled to 0°, and treated with 17.8 ml of 1N HCl. The reaction was allowed to warm to room temperature and stirred approximately 4 hours. The solvent was removed in vacuo. The residue was taken up in 30 ml of $CHCl_3$, neutralized with solid $Na_2CO_3$, filtered, dried over $MgSO_4$ and concentrated in vacuo to give 1.95 g of the title compound as a colorless oil.

E.

[2R-(2$\alpha$,3$\alpha$,4$\beta$)]-Tetrahydro-2-[(4-methoxyphenyl)diphenylmethoxy]methyl]-3,4-furandiol, 4-acetate ester Under an argon atmosphere, [2R-(2$\alpha$,3$\alpha$,4$\beta$)]-tetrahydro-3,4-dihydroxy-2-furanmethanol, 4-acetate ester (1.75 g, 9.94 mmole) was dissolved in 50.6 ml of a solution of $CH_2Cl_2$:dimethylformamide (10:1), chilled to 0°, and treated in one portion with 4-methoxytrityl chloride (3.07 g, 9.94 mmole). A solution of triethylamine (2.09 ml, 14.9 mmole) in 3 ml of $CH_2Cl_2$ was added dropwise over two minutes, with rapid stirring. The reaction was allowed to stir four hours at 0°-5°, diluted with 100 ml of $CH_2Cl_2$, washed with saturated $NaHCO_3$ (1×100 ml) and $H_2O$ (2×100 ml), and then dried over $Na_2SO_4$. The solvent was removed in vacuo and the residue was chromatographed on 200 g of silica gel, eluting with 500 ml hexane, followed by hexane:acetone (80:20). Evaporation of the solvent and drying under high vacuum providing 3.11 g of the title compound as a colorless foam.

F.

2R-(2$\alpha$,3$\alpha$,4$\beta$)]-Tetrahydro-2-[[(4-methoxyphenyl)diphenylmethoxy]methyl]-3,4-furandiol, 4-acetate, 3-methanesulfonate ester

[2R-(2$\alpha$,3$\alpha$,4$\beta$)]-Tetrahydro-2-[[(4-methoxyphenyl)-diphenylmethoxy]methyl]-3,4-furandiol, 4-acetate ester (3.11 g, 6.92 mmole) was dissolved under argon in 30 ml of dry pyridine and chilled to 0°. Methanesulfonyl chloride (1.07 ml, 13.8 mmole) was added via syringe and the reaction mixture was allowed to warm to room temperature. After five hours, the reaction mixture was poured into a mixture of ice water and chloroform, and the resulting mixture was extracted twice with chloroform. The combined organic layers were washed twice with saturated $NaHCO_3$, three times with water, and dried over anhydrous $MgSO_4$. The solvent was removed under vacuum, the residue suspended in toluene (3×), and the solvent removed under vacuum to yield 3.36 g of the title compound as a colorless foam, which was used without further purification.

G.

[2R-(2$\alpha$,3$\beta$,4$\beta$)]-3,4-Epoxytetrahydro-2-[[(4-methoxyphenyl)diphenylmethoxy]-methyl]furan 2R-(2$\alpha$,3$\alpha$,4$\beta$)]-Tetrahydro-2-[(4-methoxyphenyl)diphenylmethoxy]methyl]-3,4-furandiol, 4-acetate, 3-methanesulfonate ester (3.36 g, 6.39 mmole) was dissolved under nitrogen in 36 ml of dry methanol and treated with anhydrous $K_2CO_3$ (1.06 g, 7.67 mmole). The reaction was carefully monitored by TLC (7:3 hexane:acetone) for the disappearance of the intermediate alcohol formed by methanolysis of the acetate. After 3 hours, the formation of epoxide appeared to be complete and the solvent was removed under vacuum. The residue was partitioned between $CHCl_3$ and 5% $NaHCO_3$, and the aqueous layer was further extracted with $CHCl_3$. The organic layers were combined, dried over $MgSO_4$, and concentrated to a pale yellow syrup. Flash chromatography (200 g silica gel, 8:2 hexane:acetone) provided 2.13 g of the title compound as a white foam.

H.

[3R-(3$\alpha$,4$\beta$,5$\alpha$)]-5-Methyl-1-[tetrahydro-4-hydroxy-5-[[(4-methoxyphenyl)diphenylmethoxy]methyl]-3-furanyl]-2,4(1H,3H)pyrimidinedione

[2R-(2$\alpha$,3$\beta$,4$\beta$)]-3,4-Epoxytetrahydro-2-[[(4-methoxyphenyl)diphenylmethoxy]methyl]furan (1.05 g, 2.70 mmole, dried three times azeotropically with toluene), 18-crown-6 (607 mg, 2.29 mmole), dry thymine (1.46 g, 11.6 mmole) and NaH (60% dispersion, 64.8 mg, 1.6 mmole) were suspended in 8 ml of dry sulfolane under argon and the reaction vessel placed in a 110° oil bath.

The reaction was stirred under argon for 3.5 days at 110°. An additional 64.8 mg of 60% NaH was added, and the reaction was heated an additional 24 hours. The mixture was cooled to room temperature, treated with 15 g silica gel, slurried in 15 ml of $CH_2Cl_2$, and applied to a column of 100 g of silica gel packed in $CH_2Cl_2$. This column was eluted slowly (using gravity) with 600 ml of $CH_2Cl_2$, followed by a step gradient to 3% MeOH in $CH_2Cl_2$. The appropriate fractions were combined and the impure product was rechromatographed on 100 g of silica gel (eluting with 60:40 hexane:acetone) to yield a total of 458 mg of pure title compound.

I.

[3R-(3α,4β,5α)]-5-Methyl-1[tetrahydro-4-hydroxy-5-(hydroxymethyl)-3-furanyl]-2,4-(1H,3H)pyrimidinedione

[3R-(3α,4β,5α)]-5-Methyl-1-[tetrahydro-4-hydroxy-5-[[(4-methoxyphenyl)diphenylmethoxy]methyl]-3-furanyl]-2,4(1H,3H)pyrimidinedione (450 mg, 0.875 mmole) was dissolved in 5 ml of methanol and 5 ml of tetrahydrofuran. This mixture was treated with 2.2 ml of 1N HCl. The reaction vessel was placed in a 60° oil bath and heated at 60° for 1.5 hours under a nitrogen atmosphere. The solution was adjusted to pH 5.5. with 0.1N NaOH and the solvent was removed under vacuum. The residue was partitioned between 10 ml of $H_2O$ and 10 ml of ether. The aqueous layer was concentrated to ca. 3 ml, applied to a reverse phase chromatography column (HP-20P), and eluted with $H_2O$. Combination of the appropriate fractions provided 185 mg of the title compound as a deliquescent solid upon lyophilization.

$^1$H-NMR (270 MHz, DMSO) δ 11.25 (brs, 1H), 7.53 (s, $^1$H), 5.58 (brs, 1H), 4.89 (brt, 1H), 4.81 (m, 1H), 4.15 (m, 1H), 4.20 (dd, J=9, 6.5, 1H), 3.85 (dd, J=9, 5 Hz), 3.61–3.72 (m, 1H) 3.48–3.61 (m, 2H) 1.78 (s, 3H).

EXAMPLE 3

[3R-(3α,4β,5α)]-4-Amino-1-[tetrahydro-4-hydroxy-5-(hydroxymethyl)-3-furanyl]-2(1H)-pyrimidinone

A.

[3R-(3α,4β,5α)]-4-Amino-1-[tetrahydro-4-hydroxy-5-[[(4-methoxyphenyl)diphenylmethoxy]methyl]-3-furanyl]-2(1H)-pyrimidinone

[2R-(2α,3β,4β)]-3,4-Epoxytetrahydro-2-[[(4-methoxyphenyl)diphenylmethoxy]methyl]furan (0.920 g, 2.37 mmole, dried three times azetropically with toluene), 18-crown-6 (0.470 g, 1.78 mmole), cytosine (0.540 g, 4.86 mmole), and anhydrous potassium carbonate (0.164 g, 1.19 mmole) were suspended in 10 ml of dry sulfolane under argon. The reaction vessel placed in a 115° oil bath. The reaction was stirred under argon for 5 days at 115° and was monitored for the disappearance of epoxide by TLC (60:40 hexane: acetone) and the appearance of the desired product (80:20 $CHCl_3$:MeOH). The reaction mixture was cooled to room temperature, treated with 15 g of silica gel, slurried in 15 ml of $CH_2Cl_2$, and applied to column of silica gel (100 g) packed in $CH_2Cl_2$. This column was eluted slowly with 300 ml of $CH_2Cl_2$, followed by a step gradient of 3–9% MeOH in $CH_2Cl_2$. The pure title compound (0.650 g) was obtained as a yellowish foam.

B.

3R-(3α,4β,5α)]-4-Amino-1-[tetrahydro-4-hydroxy-5-(hydroxymethyl)-3-furanyl]-2(1H)-pyrimidinone

[3R-(3α,4β,5α)]-4-Amino-1-[tetrahydro-4-hydroxy-5-[[(4-methoxyphenyl)diphenylmethoxy]methyl]-3-furanyl]-2(1H)-pyrimidinone (0.610 g, 1.22 mmole) was dissolved in 25 ml of MeOH and treated with 6.1 ml of 1N HCl. The reaction vessel was placed in a 60° oil bath and heated at 60° for one hour under an argon atmosphere. The resulting solution was adjusted to pH 8 with 0.5N NaOH, and the solvent was removed under vacuum. The residue was partitioned between $H_2O$/ether, and the water layer was washed one more time with ether. The ether washes were back-extracted with water and the combined aqueous layers concentrated to ca. 3 ml. Reverse phase chromatography (eluting with water) provided the title compound (201 mg) as a white solid upon removal of the water under vacuum, followed by addition of methanol and concentration to dryness three times. M.P. 235° C.

$^1$H-NMR (270 MHz, DMSO) δ 7.59 (d, 1H, J=7.0 Hz), 7.00 (brs, 2H), 5.68 (d, 1H, J=7.0 Hz), 5.51 (d, 1H J=5.9 Hz), 4.79–4.85 (m, 2H), 4.04–4.13 (m, 1H), 4.00 (dd, 1H, J=7.0, 10.1 Hz) 3.76 (dd, 1H, J=4.1, 10.1 Hz) 3.48–3.67 (m, 3H), 3.17 (d, J=5.3 Hz).

EXAMPLE 4

[3R-(3α,4β,5α)]-1-[Tetrahydro-4-hydroxy-5-(hydroxymethyl)-3-furanyl]-2,4(1H,3H)pyrimidinedione

A.

[2R-(2α,3β,4β)]Tetrahydro-2-[(triphenylmethoxy)methyl]-3,4-furandiol

Triethylamine (7.8 ml. 55 mmol), trityl chloride (12.48 g, 44.8 mmol) and 4-dimethyaminopyridine (0.228 g., 1.87 mmol) were added in succession to a stirred solution of 5 g. (37.3 mmol) 1,4-anhydro-D-ribitol (Chem. Ber. 1952, 85, 1000–1007) in 45 ml. anhydrous dimethyl formamide. The resulting mixture was stirred at ambient temperature for 3 hours, warmed to 55° C. and stirred at that temperature for 5 hours. $^1$H NMR of an aliquot showed complete transformation of the starting material to the product. The reaction mixture was diluted with 300 ml methylene chloride and washed with water (3×200 ml.). The organic phase was dried over magnesium sulfate and concentrated in vacuo. The crude residue was subjected to flash chromatography (silica gel/eluted with hexane to 50% ethyl acetate in hexane, and finally 100% ethyl acetate) affording 7.1 g. (51% yield) of the title compound, $[α]_D=35.5°$ (c=1, methylene chloride).

B.

[3aR-(3aα,4α,6aα)]-Tetrahydro-4-[(triphenylmethoxy)methyl]furo[3,4-d]-1,3,2-dioxathiole, 2,2-dioxide Thionyl chloride (1.63 ml., 22.3 mmol) was added dropwise at ambient temperature to a stirred solution of [2R-(2α,3β,4β)]-tetrahydro-2-[(triphenylmethoxy)methyl]-3,4-furandiol (7.0 g., 18.6 mmol.) and triethylamine (9.1 ml., 65.2 mmol.) in 550 ml. anhydrous ether. The mixture was stirred at that temperature for 45 minutes, filtered through celite and concentrated in vacuo. The crude residue was dissolved in 200 ml. acetonitrile followed by the successive addition of $NaIO_4$ (5.97 g., 27.9 mmol.), $RuCl_3 \wedge 3H_2O$ (154.4 mg., 0.74 mmol.) and water (300 ml.). The mixture was stirred at ambient temperature for 1 hour and diluted with 500 ml. ether.

The organic layer was separated and washed with 200 ml. saturated NaHCO₃ solution, 200 ml. brine, dried over magnesium sulfate and filtered through silica gel. The filtrate was concentrated in vacuo affording 7.8 g. (96% yield) of the title compound as a white solid.

Partial ¹H NMR (CDCl₃): δ 5.48 (m,1H), 5.23 (dd, J=1.75, 6.45 Hz,1H).

C.

[3R-(3α,4β,5α)]-1-[Tetrahydro-4-hydroxy-5-[(triphenylmethoxy)methyl]-3-furanyl]-2,4(1H,3H)-pyrimidinedione A mixture of [3aR-(3aα,4α,6aα)]-tetrahydro-4-[(triphenylmethoxy)methyl]furo[3,4-d]-1,3,2-dioxathiole, 2,2-dioxide (3.5 g., 8 mmol.), uracil (4.48 g., 39.95 mmol.) and anhydrous potassium carbonate (3.31 g., 23.97 mmol.) in 225 ml. dry dimethylformamide was heated at 90° C. for 8 hours, allowed to come to room temperature, filtered and concentrated in vacuo. The residue was dissolved in 500 ml. dioxane followed by the addition of 1 ml. water and 0.25 ml. 20% H₂SO₄. After stirring the reaction mixture at room temperature for 1 hour, it was stirred for 5 minutes with magnesium sulfate and filtered through potassium carbonate. The filtrate was concentrated in vacuo and the crude residue subjected to flash chromatography (silica gel/step wise gradient from hexane to ethyl acetate) giving 1.45 g. (45% yield) of the title compound as a white foam, [α]$_D$ −30.5° (c=1, methylene chloride).

D.

[3R-(3α,4β,5α)]-1-Tetrahydro-4-hydroxy-5-(hydroxymethyl)-3-furanyl]-2,4(1H,3H)pyrimidinedione To a mixture of [3R-(3α,4β,5α)]-1-[tetrahydro-4-hydroxy-5-[(triphenylmethoxy)methyl]-3-furanyl]-2,4(1H,3H)pyrimidinedione in methanol is added a solution of 10% aqueous HCl at room temperature. The mixture is stirred at room temperature for 10 hours and then is concentrated. The residue is mixed with water and the pH is adjusted to 7 with 1N potassium hydroxide. The resulting mixture is chromatographed on HP-20P reverse phase resin to provide the title compound.

EXAMPLE 5

Treatment of Viral Infection in Cell Culture in Vitro

Assays were performed in cell culture systems to determine the concentrations of compounds that are effective in preventing several kinds of viral infections. The assays are described below, and the results are presented in Table 1.

Abbreviations:

HSV-1 (herpes simplex virus type 1, strain Schooler), HSV-2 (herpes simplex virus type 2, strain 186), VZV (varicella zoster virus, strain ELLEN).

Cell Culture Assays:

HSV-1, HSV-2, and VZV antiviral assays: Virus was adsorbed to WI-38 cell culture monolayers in 6 well culture plates (Costar, Cambridge, Mass.) for 1 hour prior to addition of maintenance medium containing duplicate dilutions of the test compound. Inhibition of plaque development was evaluated on fixed and stained monolayers after 4 days incubation at 37° C. for HSV-1 and HSV-2 and after 6–7 days incubation at 37° C. for VZV. ID₅₀ values were determined from the drug concentration which conferred at least a 50% plaque reduction compared to virus controls (Table 1).

TABLE 1

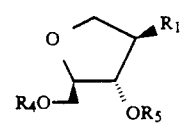

| ID₅₀ (μg/mL) for the following viruses: | | | |
|---|---|---|---|
| R₁ | HSV-1 | HSV-2 | VZV |
| (imidazole carboxamidine) | 2-5 | 2 | 50-100 |
| (methyl pyrimidinone) | 10 | >100 | >100 |
| (amino pyrimidinone) | >100 | >100 | 25-50 |

What we claim is:

1. A compound of the formula

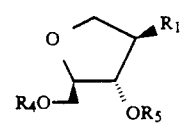

wherein the sterochemistry is absolute and is derived from the chiral precursors D-sorbitol or 1,4-andro-d-ribitol and a pharmaceutically acceptable salt thereof wherein R₁ is

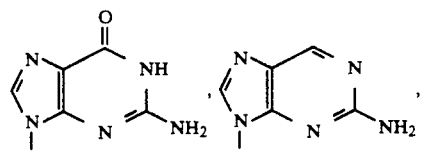

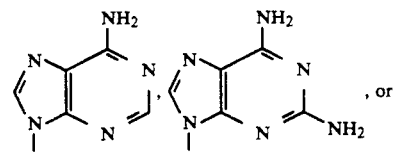

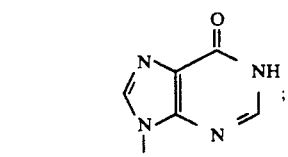

R₄ and R₅ are independently selected from the group consisting of hydrogen, —PO₃H₂, and

and

R₆ is hydrogen, alkyl, substituted alkyl or aryl wherein the term "alkyl" refers to straight or branched chain groups of 1 to 10 carbons, the term "substituted alkyl" refers to straight or branched chain alkyl of 1 to 10 carbons wherein said substituent is selected from the group consisting of halogen, amino, azido, hydroxy, cyano, trialkylammonium (wherein each alkyl group has 1 to 6 carbons), aryl, and carboxy, and the term "aryl" refers to phenyl and phenyl having one, two, or three substituents selected from the group consisting of alkyl of 1 to 6 carbons, alkoxy of 1 to 6 carbons, halogen, trifluoromethyl, amino, amido, alkylamino of 1 to 6 carbons, dialkylamino (wherein each alkyl group has 1 to 6 carbons), nitro, cyano, alkanoyloxy of 2 to 11 carbons, carboxy, carbamoyl, and hydroxy.

2. An antiviral pharmaceutical composition comprising as the active component a compound of claim 1 or a pharmaceutically acceptable salt thereof and a pharmaceutically acceptable carrier.

3. A compound in accordance with claim 1 wherein R₁ is

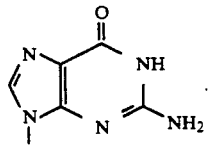

4. The composition of claim 2 wherein the active component is [3R-(3α,4β,5α)]-2-amino-1,9-dihydro-9-[tetrahydro-4-hydroxy-5-(hydroxymethyl)-3-furanyl]-6-H-purin-6-one.

5. The method of treating a herpes simplex virus type 1 or 2 or a varacella-zoster virus in a mammal which comprises administering an antiviral effective amount of the composition of claim 4.

6. A compound in accordance with claim 1 wherein R₄ and R₅ are independently hydrogen or

7. A compound in accordance with claim 1 wherein R₄ and R₅ are independently hydrogen or —PO₃H₂.

8. A compound in accordance with claim 1 wherein R₄ and R₅ are hydrogen.

9. A compound in accordance with claim 1, [3R-(3α,4β,5α)]-2-amino-1,9-dihydro-9-tetrahydro-4-hydroxy-5-(hydroxymethyl)-3-furanyl]-6H-purin-6-one.

* * * * *